United States Patent
Norman et al.

(10) Patent No.: US 9,758,593 B2
(45) Date of Patent: *Sep. 12, 2017

(54) COMPOSITIONS AND METHODS FOR TREATING COCAINE-RELATED DISORDERS

(75) Inventors: Andrew B. Norman, Cincinnati, OH (US); William J. Ball, Jr., New Richmond, OH (US); Nils Lonberg, Woodside, CA (US); Denise Williams, Livermore, CA (US)

(73) Assignees: University of Cincinnati, Cincinnati, OH (US); E. R. Squibb & Sons, L.L.C., Princeton, NJ (US)

( * ) Notice: Subject to any disclaimer, the term of this patent is extended or adjusted under 35 U.S.C. 154(b) by 2094 days.

This patent is subject to a terminal disclaimer.

(21) Appl. No.: 11/788,808

(22) Filed: Apr. 20, 2007

(65) Prior Publication Data

US 2007/0280934 A1  Dec. 6, 2007

Related U.S. Application Data

(60) Provisional application No. 60/793,604, filed on Apr. 20, 2006.

(51) Int. Cl.
*A61K 39/00* (2006.01)
*C07K 16/44* (2006.01)

(52) U.S. Cl.
CPC ........ *C07K 16/44* (2013.01); *A61K 2039/505* (2013.01); *C07K 2317/24* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,913,917 B2 * | 7/2005 | Landry | 435/188.5 |
| 2003/0077793 A1 | 4/2003 | Landry | |
| 2005/0069966 A1 * | 3/2005 | Grimes et al. | 435/7.92 |

OTHER PUBLICATIONS

Redwan et al. Biotech Bioeng 82: 612-618, 2003.*
Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1): 34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Paul, Fundamental Immunology, (textbook), 1993, pp. 292-295.*
Rudikoff et al Proc. Natl. Acad. Sci. USA 1982, 79 :1979-1983.*
Casset et al Biochemical and Biophysical Research Communications, 2003, vol. 307, pp. 198-205.*
Vajdos et al. Journal of Molecular biology, 2002, vol. 320, pp. 415-428.*
Norman et al. Jour Pharm Exp Ther 320: 145-153, 2007.*
ACS Publications—Ethical guidelines (revised Jun. 2012).*
Paula et al, Three Dimensional Quantitative Structure-Activity Relationship Modeling of Cocaine Binding by a Novel Human Monoclonal Antibody, J. Med. Chem., 2004, 47, 133-142.

* cited by examiner

*Primary Examiner* — Daniel E Kolker
*Assistant Examiner* — Aditi Dutt
(74) *Attorney, Agent, or Firm* — Dinsmore & Shohl LLP

(57) ABSTRACT

Methods for treating a cocaine-related disorder in an individual include administering to the individual a therapeutic amount of an antibody comprising a human immunoglobulin gamma heavy chain and a murine lambda light chain. In another embodiment, the light chain includes a human kappa light chain at least partially derived from 1B3. Other embodiments are directed toward the antibodies themselves and methods of binding the antibodies.

16 Claims, 4 Drawing Sheets

COMPOSITIONS AND METHODS FOR TREATING COCAINE-RELATED DISORDERS

CROSS-REFERENCES TO RELATED APPLICATIONS

This application claims the benefit of U.S. Provisional Application No. 60/793,604, filed Apr. 20, 2006.

FIELD OF THE INVENTION

The present invention is directed to methods and compositions relating to monoclonal antibodies.

BACKGROUND OF THE INVENTION

Cocaine is a powerfully addictive stimulant that directly affects the brain. Cocaine, however, is not a new drug. In fact, it is one of the oldest known drugs. The pure chemical, cocaine hydrochloride, has been an abused substance for more than 100 years, and coca leaves, the source of cocaine, have been ingested for thousands of years.

Today, cocaine use ranges from occasional use to repeated or compulsive use, with a variety of patterns between these extremes. There is no safe way to use cocaine and any route of administration can lead to absorption of toxic amounts of cocaine, leading to acute cardiovascular or cerebrovascular emergencies that could result in sudden death. Repeated cocaine use by any route of administration can produce dependence, addiction and other adverse health consequences.

Despite decades of basic and clinical research there are currently no medications available to treat cocaine dependence, addiction, overdose or to help prevent relapse. Thus, therapies are needed which can treat such cocaine-related disorders.

SUMMARY OF THE INVENTION

One embodiment of the present invention is directed toward a method for treating a cocaine-related disorder in an individual. The method includes administering to the individual a therapeutic amount of an antibody comprising a human gamma heavy chain and a murine lamda light chain.

In another embodiment, the present invention is directed toward a method for treating a cocaine-related disorder in an individual. The method comprises administering a therapeutic amount of an antibody comprising a human gamma heavy chain and a human kappa light chain at least partially derived from 1B3.

In another embodiment, the present invention is directed toward a monoclonal antibody comprising a human gamma heavy chain and a murine lambda light chain.

In another embodiment, the present invention is directed toward a monoclonal antibody comprising a human gamma heavy chain and a human kappa light chain at least partially derived from 1B3.

In an additional embodiment, the present invention is directed toward a method for binding cocaine or a derivative thereof. The method includes contacting cocaine or a derivative thereof with an effective amount of an antibody, wherein the antibody comprises a human gamma heavy gamma chain and a light chain, wherein the light chain is selected from the group consisting of: a murine lambda light chain, a human kappa light chain derived at least partially from 1B3, and combinations thereof.

These an additional embodiments of the invention will be more fully apparent in view of the following detailed description.

BRIEF DESCRIPTION OF THE DRAWINGS

The following detailed description will be more fully understood in view of the drawings in which.

Figure 1:
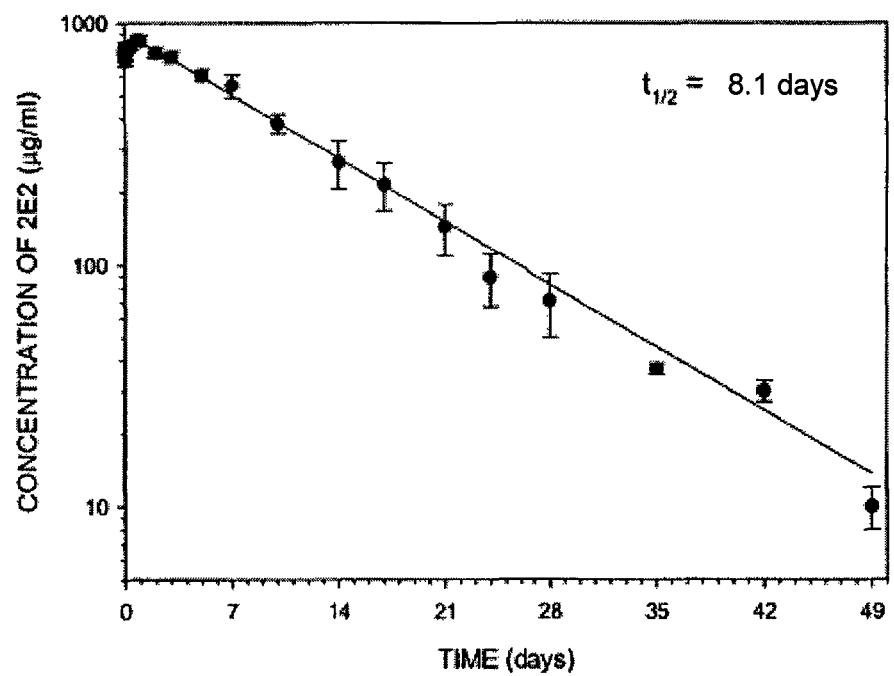
FIG. 1 is a graph which depicts pharmacokinetics of an anti-cocaine mAb 2E2 where mice receive an i.v. infusion of 120 mg/kg of 2E2, samples of blood (10 µl) are obtained from tail veins at the indicated times after the completion of the mAb infusion, and concentrations of 2E2 in blood are determined using an ELISA; data points represent the mean±SEM from 8 mice, the Vdss is approximately 0.28 l/kg and a single compartment model with a $t_{1/2}$ of 8.1 days adequately describes the elimination phase, represented by the best-fit regression line through the data points.

The embodiments set forth in the drawings are illustrative in nature and are not intended to be limiting of the invention defined by the claims. Moreover, individual features of the drawings and the invention will be more fully apparent and understood in view of the detailed description.

DETAILED DESCRIPTION

As used herein, "cocaine-related disorders" include cocaine dependence, addition, overdose and/or relapse, and any other disorder resulting in whole or in part from cocaine use. As the site of action of cocaine is in the brain, decreasing the concentrations reaching the brain would be expected to decrease the probability of dependence, addiction, overdose, and relapse. Antibodies with high affinity and specificity for cocaine would be expected to act as pharmacokinetic antagonists by sequestering cocaine in the peripheral circulation and preventing its entry to the brain. Indeed, active immunization of animals with hapten-carrier conjugates can elicit the production of polyclonal anti-cocaine antibodies with sufficient levels and affinity for cocaine that they can reduce the amount of cocaine entering the brain. Active immunization has also been shown to attenuate the behavioral effects and the priming effect of systemically administered cocaine in rats. Furthermore, the ability of active immunization to produce levels of polyclonal anti-cocaine antibodies in humans that were associated with a decrease in use of cocaine demonstrates the potential efficacy of immunotherapy for cocaine abuse. Unfortunately, individuals with compromised immune systems (like those who have clinically induced immunosuppression or those who suffer from some sort of an infection) can often not be actively immunized due to the risks of developing a complication from the active immunization. Often, those individuals who are suffering from cocaine-related disorders also have compromised immune systems.

An alternative to active immunization is passive immunization. In passive immunization, a pre-made antibody is given to the individual. While this process is usually short lasting (a few days or even a few weeks), it is much safer and effective for those with compromised immune systems. In addition, using a monoclonal antibody (mAb) with a defined affinity, specificity and dose may be even more efficacious than active immunization. Indeed, passive immunization with non-human anti-cocaine mAbs attenuates the behavioral effects of cocaine and therefore represents an alternative or adjunct to active immunization.

Previously, a murine anti-cocaine antibody (GNC92H2) was generated and demonstrated to have in vivo efficacy in rat models of cocaine addiction. Also, two catalytic murine anti-cocaine mAbs that are designed to reduce blood cocaine levels through its hydrolysis have been generated and characterized. Unfortunately, non-human sequence anti-cocaine mAbs would be expected to elicit an immune response in humans similar to that elicited by the murine mAb OKT-3 used for immunosuppression for organ transplant procedures. This immune response will target and try to destroy the non-human mAB thus decreasing or neutralizing the long-term efficacy of such an immunotherapeutic agent. Furthermore, the antibody affinity for cocaine should also be a major determinant of clinical efficacy. Unfortunately, the affinities of the catalytic mAbs for cocaine are reported to be approximately 220 µM and 55-5,240 µM, while the affinity of the anti-cocaine mAb GNC92H2 is reported to be 200 nM. Therefore, a more efficacious and predominantly human antibody is likely to decrease the probability of inducing a neutralizing immune system response. This theory led to the generation and characterization of a monoclonal antibodies which are at least partially generated in transgenic mice that produce human sequence mAbs.

In contrast to the affinities of the catalytic and non-human mABs, the affinity of these new antibodies for cocaine is approximately 4 nM, which is considerably higher than that of other anti-cocaine mAbs currently under study. Additionally, these antibodies have high specificity for cocaine over the major metabolites of cocaine. Therefore, these antibodies have important physicochemical properties that confer efficacy as a passive immunotherapeutic agent.

Therefore, according to one embodiment, the present invention is directed toward a monoclonal antibody comprising a human gamma heavy chain and a murine lamda light chain. In one embodiment, the murine lambda light chain comprises SEQ ID NO: 1 or a derivative thereof. In another embodiment, the human gamma heavy chain comprises SEQ ID NO: 2. In a further embodiment, the human gamma heavy chain comprises SEQ ID NO: 2 and the murine lambda light chain comprises SEQ ID NO: 1. In one embodiment, the combination of these sequences is known as 2E2. In another embodiment, the antibody comprises a human gamma heavy chain and a human kappa light chain derived at least partially from 1B3. In another embodiment, the antibody is an immunoglobulin.

According to another embodiment, the invention is directed toward a method of treating a cocaine-related disorder in an individual. The method includes administering a therapeutic amount of an antibody to the individual including a human immunoglobulin gamma heavy chain and a murine lambda light chain. The human gamma heavy chain contains the majority of the specificity for cocaine and its derivatives and thus it may be used in combination with any light chain which effects a therapeutic effect for cocaine-related disorders.

In one embodiment, the human gamma heavy chain comprises SEQ ID NO: 2 or a derivative thereof. In an additional embodiment, the light chain comprises a murine lambda light chain including SEQ ID NO: 1 or a derivative thereof. In one embodiment, the murine lambda light chain is partially murine derived. In further embodiment, the partially murine derived light chain comprises a murine variable region and a human constant region. Derivatives as employed herein include those sequences which would be functionally equivalent to either chain of the antibody. This would include those antibodies which have the same primary structure (i.e. sequence), but have a different tertiary structure due to the addition of, for example, a salt or a sugar. In addition, the functional regions of the sequences have been identified as the variable regions. Thus, heavy and/or light chains including at least one variable region and maintaining their ability to be therapeutic for cocaine-related disorders are also included. In the murine lambda light chain, there are three variable regions. These regions reside at amino acid residues numbered 23-36 (SEQ ID NO: 4), 52-58 (SEQ ID NO: 5), and 91-99 (SEQ ID NO: 6) of SEQ ID NO: 1. In the human gamma heavy chain, these regions reside at amino acid residues numbered 31-36 (SEQ ID NO: 7), 50-66 (SEQ ID NO: 8), and 99-102 (SEQ ID NO: 9) of SEQ ID NO: 2. In the human kappa light chain, these regions reside at amino acid residues numbered 24-34 (SEQ ID NO: 10), 50-56 (SEQ ID NO: 11), and 89-98 (SEQ ID NOS: 12 and 13) of SEQ ID NO: 3.

The variable regions or CDR regions are the sites for ligand-antibody interactions. Thus, in one embodiment, derivatives of SEQ ID NO: 1 may comprise one or more of SEQ ID NOS: 4, 5, and 6 and derivatives of SEQ ID NO: 2 may comprise one or more of SEQ ID NOS: 7, 8, and 9. Additionally, derivatives of the variable regions could also be used, for example derivatives having between 90-95%, 85-90%, 80-85%, 75-80%, 70-75%, 65-70%, or 60-65% homology to their respective variable region sequences. The resulting antibodies from the derivatives of the variable regions also have the same cocaine binding functionality as the other disclosed antibodies.

In an additional embodiment, a method for treating cocaine-related disorders includes administering a therapeutic amount of an antibody comprising a human immunoglobulin gamma heavy chain and a human kappa light chain at least partially derived from 1B3 to an individual. This light chain is selected because this sequence has been shown by sequencing of genomic DNA to be generated by light chain gene recombination in the hybridoma cell line 2E2 that produces mAb 2E2. The anti-digoxin mAb 1B3 is a fully human sequence mAb that binds digoxin and digitoxin with high affinity (nMolar). This antibody has been described in two publications. Farr, C. et al., "Three-dimensional Quantitative Structure-Activity Relationship Analysis of Human Sequence Antidigoxin mAbs using CoMFA." Journal Medicinal Chemistry 45 (15): 3257-3270, 2002 and Paul, S., Monson, N. & Ball, W. J., "Molecular Modeling of Cardiac Glycoside Binding by the Human sequence mAb 1B3." Proteins: Structure, Function and Bioinform. 60: 382-391, 2005, incorporated herein by reference. In one embodiment, the human light kappa chain comprises SEQ ID NO: 3 (1B3a) or a derivative thereof. In another embodiment, the human kappa light chain comprises SEQ ID NO: 14 (1B3b) or a derivative thereof. In one embodiment, derivatives of SEQ ID NOS: 3 and 14 may comprise one or more of SEQ ID NOS: 10-13. Additionally, derivatives of their CDR regions are also applicable as described above for SEQ ID NOS: 1 and 2.

In another embodiment, an antibody binds cocaine or a derivative thereof. Radioligand binding assays using an antibody and [$^3$H]-cocaine yields an average dissociation constant ($K_d$) of 4.4 nM. Binding inhibition constants ($K_i$) of the cocaine derivatives are determined by competition assays with a constant [$^3$H]-cocaine concentration and varying concentrations of nonradioactive competitors. The results show that the present antibodies bind cocaethylene with an affinity ($K_i$=3.4 nM) nearly identical to that for cocaine. On the other hand, the affinities for the three physiologically important but inactive cocaine derivatives benzoylecgonine, ecgonine methyl ester, and ecgonine are significantly lower ($K_i$ values of 43 nM, 5.2 µM and 95 µM, respectively), revealing the importance of the benzoyl moiety for high binding affinity. Even $K_d$ values of 40 nM show beneficial results. Other examples of cocaine derivatives include: (−) cocaine; cocaine propyl ester; RTI-128; RTI-66; RTI-160; RTI-192; m-hydroxycocaine; WIN 35,065-2; WIN 35,428; RTI-31; RTI-32; RTI-55; RTI-111; m-hydroxybenzoylecgonine; p-hydroxybenzoylecgonine; RTI-113; tropine; benztropine; 4',4"-difluoro-3α-diphenylmethoxytropane; hyoscyamine-N-oxide; methylanisotropine; tropisetronmethiodide; anisodine; scopatamine; scopatamine-N-oxide; methylscopolamine; N-butylscopolamine; (−) pseudococaine; (+) cocaine; norcaine; benzoylnorecgonine; (+) pseudococaine; ecgonidine; exo-6-hydroxytropinone; and methylcocaethylene.

The monoclonal antibodies of the present invention use their binding affinity for cocaine and its derivatives to reduce the concentration of cocaine or its derivatives in the brain. Infused antibodies also produce a dramatic dose-dependent increase in plasma cocaine concentrations and a concomitant decrease in the brain cocaine concentrations produced by an i.v. injection of cocaine HCl (0.56 mg/kg). At the highest dose of antibody tested (3:1, mAb:drug), cocaine is not detectable in the brain. Pharmacokinetic studies show that the normal disappearance of cocaine from plasma is described by a 2-compartment pharmacokinetic model with distribution $t_{1/2\alpha}$ and terminal elimination $t_{1/2\beta}$ values of 1.9 and 26.1 min, respectively. In the presence of an equimolar dose of mAb 2E2 there is a 26-fold increase in the area under the plasma cocaine concentration-time curve (AUC) relative to the AUC in the absence of 2E2. Consequently, the antibodies of the present invention decrease cocaine's volume of distribution from 6.0 l/kg to 0.20 l/kg, which approximates that of 2E2 (0.28 l/kg). However, cocaine is still rapidly cleared from plasma and its elimination is now described by a single compartment model with an elimination $t_{1/2}$ of 17 min. Importantly, the antibodies also produce a 4.5-fold (78%) decrease in the cocaine AUC in the brain. Therefore, the effect of the antibodies on plasma and brain cocaine concentrations is predominantly due to a change in the distribution of cocaine with negligible effects on its rate of clearance.

In addition to being a monotherapy, embodiments also include additional co-therapies. For example, when treating someone in rehabilitation to prevent relapse, an antibody according to the invention can be administered in conjunction with treatments for withdrawal symptoms (for example, administration of amantadine and propranolol). An antibody according to the invention can be used in conjunction with counseling and other forms of psychotherapy. In addition, it can be used with any antagonist or agonist pharmacotherapies that use compounds for which the antibody does not have substantial affinity. The antibody can also be used with other antibodies that target other drugs of abuse or medicaments.

An antibody according to the present invention may be administered by any suitable route or device. In one embodiment, the antagonist will be administered by injection. The most common form of delivery will be an intravenous injection or infusion.

The antibody is administered in an amount sufficient to treat the cocaine-related disorder. The treatment as used herein encompasses a reduction in clinical symptoms of the disorder and/or elimination of the disorder. Therapeutic amounts will vary based on an individual's age, body weight, symptoms, and the like, and may be determined by one of skill in the art in view of the present disclosure. Initial clinical studies of a cocaine vaccine do provide vital information about the concentrations of anti-cocaine antibodies required to decrease cocaine use by cocaine abusers. In vaccinated patients the highest mean serum antibody titer would correspond to about 61.4 µg/mL, and a decrease in cocaine use is reported in this cohort as well as cohorts with lower mean antibody titers. As the standard blood volume in a 70 kg person is 2.8 liters, then the quantity of anti-cocaine antibodies that confer efficacy in patients is about 61.4 µg/mL×2,800 ml or about 172 mg/person (about 2.5 mg/kg). This is likely be a minimally effective dose. By comparison, doses of 40 and 120 mg/kg can be safely administered and are efficacious in rodent models. These doses translate to 2,800-8,400 mg in a 70 kg person, almost 20-50-fold higher than may be required to confer efficacy in humans. Additionally, it should be noted that the polyclonal anti-cocaine antibodies that constituted the standard immune response in vaccinated patients had an average affinity (Kd) of 28 nM [17], while the present anti-cocaine monoclonal antibodies have a higher affinity (for example, 2E2 has a Kd=4 nM). Therefore, equimolar doses of 2E2 are more effective or equieffective doses would be lower.

In addition to its use as a treatment for cocaine-related disorders, the antibodies of the current invention could also be used in screening assays for the development of other therapeutics, including other therapeutics useful for the treatment of cocaine. Thus, one embodiment of the present invention also includes a method for binding cocaine or a derivative thereof. The method comprises contacting cocaine or a derivative thereof with an effective amount of an antibody. The antibody comprises a human gamma heavy chain and a light chain. In one embodiment, the light chain is selected from the group consisting of: a murine lambda light chain, a human kappa light chain at least partially derived from 1B3, and combinations thereof. Additionally, as described above, the heavy and light chains can be several different combinations and/or variations.

The following examples demonstrate various specific embodiments of the invention.

EXAMPLES

Methods

Animals.

Jugular vein catheterized male Swiss-Webster mice (22-28 g at the start of the studies) are purchased. Mice are housed individually with free access to food and water and kept on a 12 h light/dark cycle. These studies are carried out in accordance with the Guide for the Care and Use of Laboratory Animals under a protocol approved by the Institutional Animal Care and Use Committee at the College of Medicine, University of Cincinnati.

Cocaine Pharmacokinetic Studies.

Prior to the start of the studies, the patency of the venous catheters is verified by demonstrating the ability to withdraw blood or inject normal saline via the catheter. The antibody (3-5 mg/ml) in phosphate-buffered saline (PBS) or vehicle (PBS) is infused at a rate of approximately 0.35 ml/min for up to two min, depending on the antibody concentration and the body weight of the animal, with the animal held under mild restraint. One hour after completion of the infusion of mAb, cocaine HCl (0.56 mg/kg) plus heparin (400 units/kg) is injected intravenously through the same catheter at a volume of 4.0 ml/kg body weight. At most sampling times, sodium pentobarbital (45 mg/kg, i.p) is administered three minutes prior to sacrificing the animal. For the 0.75 min time point the cocaine is injected into anesthetized mice. At the designated times after the injection of cocaine, anesthetized mice are sacrificed by decapitation and trunk blood (typically 0.8-1.2 ml) is collected in a 1.5 ml polypropylene microcentrifuge tube containing 11.2 µl heparin (1.0 unit/µl) and NaF (16 mg/0.8 ml of blood) to inhibit, respectively, blood coagulation and enzymatic hydrolysis of cocaine. The blood samples are centrifuged at 5,000×g for 3 min, then the plasma (typically 0.4-0.8 ml) is carefully separated from packed red blood cells, placed into sterile 1.5 ml Eppendorf microcentrifuge tubes, rapidly frozen on dry ice and then stored at −80° C. until analysis.

At the same time a separate sample of blood (approximately 100 µl) is collected from each mouse and rapidly frozen on dry ice then stored at −80° C. The concentration of hemoglobin and, where appropriate 2E2, is measured in these samples.

The whole brain is quickly removed from the decapitated mice, surface blood is blotted away, and the brain is placed in a polypropylene tube, rapidly frozen on dry ice and then stored at −80° C. until analysis. For analysis, brains are weighed and cold deionized, distilled water added to produce a total volume of 1 ml, then homogenized and centrifuged at 13,000 rpm for 45 min at 4° C. The resulting supernatants (0.4-0.6 ml) are collected into sterile polypropylene microcentrifuge tubes and an aliquot (0.05-0.40 ml) is processed for cocaine/metabolite analysis by GC/MS and hemoglobin content. Any remaining sample is stored at −80° C.

Determination of Blood and Brain Hemoglobin Concentrations.

The hemoglobin contents of brain and blood are quantified spectroscopically by combining the method reported by Choudhri et al. (1997) and a protocol provided by Pointe Scientific, Inc. (MI). In this procedure, 10 µl aliquots of blood or 50 µl aliquots of brain homogenate supernatants are diluted with 90 µl hemoglobin reagent (0.6 mM $K_3Fe(CN)_6$, 0.7 mM KCN) in glass test tubes. The reaction is allowed to proceed at room temperature for 15 min with gentle mixing. When the reaction is complete, aliquots from the standards and samples are all transferred into PVC microtiter plate wells and the absorbance is measured at a wavelength of 490 nm for the measurement of cyanmethemoglobin formation. For the similarly prepared hemoglobin standards, the absorbance is directly proportional to the hemoglobin concentration over the range used (0.3-12 g/dl). The standard curve is verified using control standards and the hemoglobin concentration in each sample is determined by comparison with the standard curve. The mean±SEM concentration of hemoglobin in whole blood and brain are determined to be 8.90±0.32 g/dl and 0.22±0.04 g/dl, respectively. The average hemoglobin content in brain tissue relative to that present in whole blood is, therefore, approximately 2.5%.

2E2 In Vivo Pharmacokinetic Studies:

Sample preparation. Mice, while under mild restraint, are administered mAb 2E2 (120 mg/kg, at 4.2 mg/ml in PBS) via an intravenous infusion over a 2 min period. Then at varying times, to obtain blood samples for mAb quantification, the mice are anesthetized using isoflurane and a sterile 27-gauge hypodermic needle or, alternatively, a sterile scalpel blade is used to puncture or make a small cut in a tail vein and 10 µl of blood is collected using a heparinized capillary pipette tip. The blood is immediately placed in a 1.5 ml polypropylene microcentrifuge tube containing 40 µl of 0.1 M sodium citrate/0.1% sodium azide pH 4.75. These samples are then rapidly placed on ice and then stored at 4° C. until use. A blood sample is taken immediately prior to the infusion of 2E2 and then at 3, 15 and 30 min, 1, 2, 4 and 8 hr, 1 day and periodically up to 49 days as shown in the results.

mAb 2E2 Quantification:

ELISA. The in vivo concentrations of 2E2 are determined using an enzyme-linked immunosorbent assay (ELISA) that compares the quantity of mAb in varying dilutions of the mouse blood samples to that quantified in a standard curve generated using known dilutions of purified 2E2 or human IgG. Briefly, the conjugate benzoylecgonine-ovalbumin (3 µg/ml, 100 µl/well) in 1 mM EGTA pH 7.4 is adsorbed onto PVC 96-well microtiter plates for 1 hr. The plates are then washed 3 times with, and all wells exposed for 10 min to, 0.5% BSA in TBS (10 mM Tris, 140 mM NaCl and 0.02% $NaN_3$, pH 6.9) in order to block non-specific protein binding. The second layer, 100 µl/well of the blood samples diluted (1:500) into BSA-TBS, is added and the sample is incubated for 2 hr. Serving as quantitation standards, duplicate 100 µl/well samples of human IgG or 2E2 diluted over a range of concentrations from 0.003-3.0 µg/ml are also similarly plated and incubated. The plates are washed with a Solution A, containing 0.5% BSA, 10 mM sodium phosphate, 145 mM NaCl, 1.5 mM MgCl$_2$, 0.05% triton X-100 and 0.02% NaN$_3$, pH 7.2. Then 50 µl/well of affinity-purified biotinylated goat anti-human IgG diluted 1:500 in Solution A is added and incubated for 1 hr. After washing, 50 µl/well of streptavidin-alkaline phosphatase, diluted (1:200) in Solution A, is added, incubated for 1 hr and removed. Then 50 µl/well of the colorimetric reaction mixture, comprised of the substrate para-nitrophenylphosphate (1 mg/ml) in substrate buffer (50 mM Na$_2$CO$_3$, 50 mM NaHCO$_3$ 1 mM MgCl$_2$ at pH 9.8), is added. After 6-8 min the reaction is stopped with 1M sodium hydroxide (50 µl/well). All steps are performed at room temperature. The reaction endpoint is measured with an ELISA reader at a wavelength of 405 nm. Each determination is done in duplicate.

Antibodies:

The hybridoma cell line secreting mAb 2E2 is generated using standard hybridoma technology by fusing spleenocyctes obtained from a transgenic mouse, strain HCo7/Ko5, following its immunization with benzoylecgonine (BE) coupled to 1,4-butanediamine-derivatized keyhole limpet hemocyanin (KLH) with the mouse cell line P3X63-Ag8.653. Production of mAb 2E2 is accomplished by growing hybridomas in severe combined immunodeficient (SCID) mice and collecting the ascites fluid. The hybridoma-secreted mAb is purified from ascites by sodium sulfate precipitation and a several step protein A-Sepharose column chromatography procedure adapted from that previously described. Identification of the full length amino acid sequences of the polyacrylamide gel separated heavy and light chains of the 2E2 molecule is accomplished using liquid chromatography/mass spectroscopy (LC/MS/MS) analysis of their tryptic fragments. The heavy (H) chain is identified as a γ$_1$ protein of the human VH3 family gene DP-50. The light (L) chain is identified as a mouse λ VL2. The MS sequencing is consistent with and confirmed results obtained previously from Edman degradation NH$_2$-terminal sequencing of the Western blotted H and L chains as well as the sequencing of mRNA-dependent cDNA representing the 2E2, V$_H$ and V$_L$ chain regions. The γ1 human H chain NH$_2$-terminal sequence is: EVQLVESGGGLVKPGG-SLRL-(see SEQ ID NO: 2), while the mouse λ chain NH$_2$-terminal sequence is: QAVVT/IQESALTTSPGGTV-(see SEQ ID NO: 1). Although the 2E2 hybridoma contains the recombined DNA sequence for a human κ L6 light chain, and this is consistent with the human κ chains of anti-digoxin antibodies generated from these transgenic mice in previous work, the L chain for the mAb expressed and used is a murine λ. These results are consistent with a recent report that hybridomas from the HCo7/Ko5 strain of transgenic mouse can generate mixed-chain, human H, mouse L mAbs in addition to human sequence mAbs. Overall, 2E2 has about an 87% sequence identity/homology with human IgG(λ)1 immunoglobulins.

The murine anti-cocaine mAb 3P1A6 obtained from BioDesign International, Inc., (Saco, Me.) has previously been reported to have a high affinity (K$_d$=0.2 nM) for cocaine and approximately 12-fold and 1,500-fold lower affinities for the inactive metabolites benzoylecgonine (BE) and ecgoninemethylester (EME), respectively. The murine anti-cocaine mAb B4E10 has been determined to have a moderate affinity for cocaine (K$_d$=40 nM) and approximately 30-fold and 50,000-fold lower affinities for BE and EME, respectively. Therefore, the murine mAbs and 2E2 have similar specificities for cocaine over its major metabolites, but an approximately 200-fold range difference for cocaine affinity. As an additional control, to test for non-specific in vivo effects resulting from infusion of mAb, non-specific human polyclonal IgG immunoglobulin is administered to mice. These latter immunoglobulins have no measurable affinity for cocaine or its major metabolites (data not shown).

Solid Phase Extraction of cocaine and metabolites from plasma and brain. In order to determine in vivo concentrations of cocaine and its metabolites BE and EME, following the i.v. injection of cocaine, 100-400 µl samples of heparinized/NaF treated plasma and 400 µl samples of brain homogenates obtained from cocaine-treated animals are added to 2 ml of 0.1 M Na phosphate buffer, pH 6.0. This is followed by the addition of 5% trichloroacetic acid at a volume equal to that of the experimental sample (100-400 µl). These mixtures are shaken for 20 minutes and then centrifuged for 15 min at 7000 rpm, all at room temperature, in order to precipitate the denatured protein. The supernatants are collected and adjusted to pH 5.4 with 10 M NaOH. Then to serve as internal standards for establishing the identification of cocaine and its metabolites as well as for normalization of the recovery of cocaine/metabolites from the mouse samples, 50 µl of a sample containing deuterated (D$_3$) cocaine-D$_3$, BE-D$_3$ and EME-D$_3$ (each at 1 µg/ml) is added to all of the experimental and the standard control samples before their undergoing solid-phase extraction/column elution. Duplicate, standard control tubes (2 ml) are also prepared containing; 0.1 M Na phosphate buffer, 50 µl of the internal standards D$_3$ cocaine/BE/EME (1 µg/ml, each), 200 µl of normal mouse plasma and varying amounts of cocaine (1-500 ng) and used to generate the standard cocaine concentration curves. Similarly, standard concentration curves are also generated for BE and EME. Also 10 µl of the stock solution of cocaine HCl (0.139 mg/ml) that is infused into the mice is also mixed with the phosphate buffer and the cocaine-D$_3$/metabolite-D$_3$ standards for quantification of the cocaine administered to the animals. Thus, the cocaine/metabolite levels are determined relative to that of standard samples undergoing the same column extraction, elution and derivatization procedures.

The procedure of Varian is used to extract and recover cocaine/metabolites from the plasma and brain samples and standards. First, Bond Elut Certify columns with the non-polar C8 sorbent, set in a Varian vacuum manifold are conditioned by washing with 2 ml methanol, followed by 2 ml of 0.1 M Na phosphate buffer, pH 6.0. Next, the prepared plasma and brain homogenate samples (2 ml) are loaded onto the Bond Elut columns. The columns are then washed with 6 ml of deionized water, 3 ml of 0.1 M HCl, and 9 ml of methanol. The column-bound analytes are then eluted with 2-3 ml of a freshly prepared solution of dichloromethane:2-propanol:ammonium hydroxide (mixed: 78:20:2, v/v/v). These extracts are then evaporated to dryness under nitrogen at 45° C. for 15 min. The residue samples are derivatized with 25 µl N-methyl-N-trimethylsilyl trifluoroacetamide (MSTFA) mixed with 25 µl ethyl acetate. These samples are vortexed and incubated at 65° C. for 30 min. After cooling, the trimethylsilyl-derivatized samples are transferred to glass autosampler vials for analysis by GC/MS. The GC/MS analysis of analytes is typically completed within 1-2 hours of sample derivatization. Analyses carried out more than eight hours after derivatization are discarded.

Gas Chromatography/Mass Spectrometry.

The gas chromatograph/mass spectrometer (GC/MS) consisted of a Shimadzu GC 17A series GC, interfaced with a Shimadzu QP-5050A quadruple MS fixed in an electron impact ionization mode with selective ion monitoring. The GC/MS is operated with a transfer line temperature of 280°

C. and a source temperature of 280° C. The MS is calibrated on a daily basis using perfluorotributylamine. The electron multiplier voltage is set at 1.2 kV. Chromatographic separation is achieved using a Restek Rtx-5MS cross linked 5% diphenyl-, 95% dimethylsiloxane capillary column (30 m×0.25 mm i.d, 0.25 μm film thickness). Helium is the carrier gas and used at a flow rate of 1.0 ml/min.

A Shimadzu AOCs autosampler is used to inject 2 μl of extract sample into the GC/MS. The GC, equipped with split/splitless injection port, is operated at 280° C. in the splitless mode with a high pressure injection set at 150 kPa for 0.75 min. The oven temperature profile is established as follows: the initial temperature is 100° C. and it is held for 1 min, then increased at a rate of 20° C./min up to 320° C. This temperature is held for 8 min resulting in a total run time of 20 min. The lower limits of cocaine/BE/EME detection ranged from 1-5 ng/ml and the linear dynamic range for most analytes is 1-3000 ng/ml. The instrument performance is evaluated by analysis of the calibrator and control samples. Analytes are identified and their concentrations are determined using both the internal deuterated standards and concentration control samples prepared with normal mouse serum, respectively, as described above. The response factor is determined for each analyte. The response factor is calculated by dividing the area of the analyte peak by the area of the internal standard peak. Calibration curves are then prepared by plotting a linear regression of the analyte/internal standard response factor versus the analyte concentration for all calibrators analyzed. The standard curve is constructed using a set of cocaine/metabolite samples varying over a concentration range of 1-500 ng/ml. The standard curve is used to determine concentrations of analytes in both control and experimental samples.

Chemicals Reagents and Reference Standards:

Standard solutions of cocaine, BE and EME (each 1 mg/ml) are prepared in methanol or acetonitrile and serve as stock solutions for preparing the reference standard curves. The cocaine-$D_3$, BE-$D_3$ and EME-$D_3$ are used as the internal standards (0.1 mg/ml each in methanol or acetonitrile). MSTFA is the derivatizing reagent. Normal mouse plasma with heparin is obtained. The human hemoglobin standards and control standards are obtained. All other chemicals and immunoreagents are purchased. All reagents and organic solvents are of analytical grade or HPLC grade.

Data Analysis and Statistics:

Cocaine and 2E2 pharmacokinetic data are analyzed using the program WinNonLin. The program provides Akaike Information Criterion (AIC) and Schwartz Bayesian Criterion (SBC) measures of "goodness of fit" of the data to the one or two compartment pharmacokinetic models that are used. Data are first analyzed according to a single compartment pharmacokinetic model. In some experiments a single compartment model gave a poor fit to the cocaine pharmacokinetic data, as assessed by a systematic deviation of the model from the data. In these cases the fit to the data is improved by applying a two compartment pharmacokinetic model that assumes cocaine distributed between a central and a peripheral compartment. In addition to an improvement in the AIC and SBC measures, the improvement of the fit of the model to the data is evaluated by a lack of a systematic deviation from the data points and a concomitant reduction in the sum of squares residuals. Applying pharmacokinetic models that assumed that cocaine distributed between more than two compartments only slightly improved the fit to the observed data and this additional complexity is considered unnecessary. Statistical comparisons of the cocaine and metabolite levels observed in the presence and absence (vehicle) of antibody at the single 5 min time point used non-parametric Mann-Whitney test while the Analysis of Variance (ANOVA) procedure is used to compare the results obtained over different experimental days.

Results

The Pharmacokinetics of mAb 2E2.

In determining the pharmacokinetics of mAb 2E2 in mice, the first samples of tail vein blood are taken 3 minutes after completion of the i.v. infusion of 2E2 (120 mg/kg) via the jugular vein of mice. The initial mean±SEM blood concentration of mAb is determined to be 370±17 μg/ml (n=8 mice). As shown in FIG. 1 there is no evidence for an initial decrease in blood concentrations over the first 24 hours. Indeed, 2E2 concentrations increased slightly over the first four hours and then appeared to plateau for approximately 20 hours. The mean concentration of 2E2 as measured 24 hours after infusion is 422±21 μg/ml. After 24 hours, the concentrations of 2E2 in blood then begin to decline and this is adequately described by a single compartment pharmacokinetic model with an elimination $t_{1/2}$ of 8.1 days (FIG. 1). This model gives a calculated volume of distribution at steady state (Vdss) for 2E2 in this group of mice of 0.28 l/kg.

The Plasma Pharmacokinetics of Cocaine.

Figure 4:
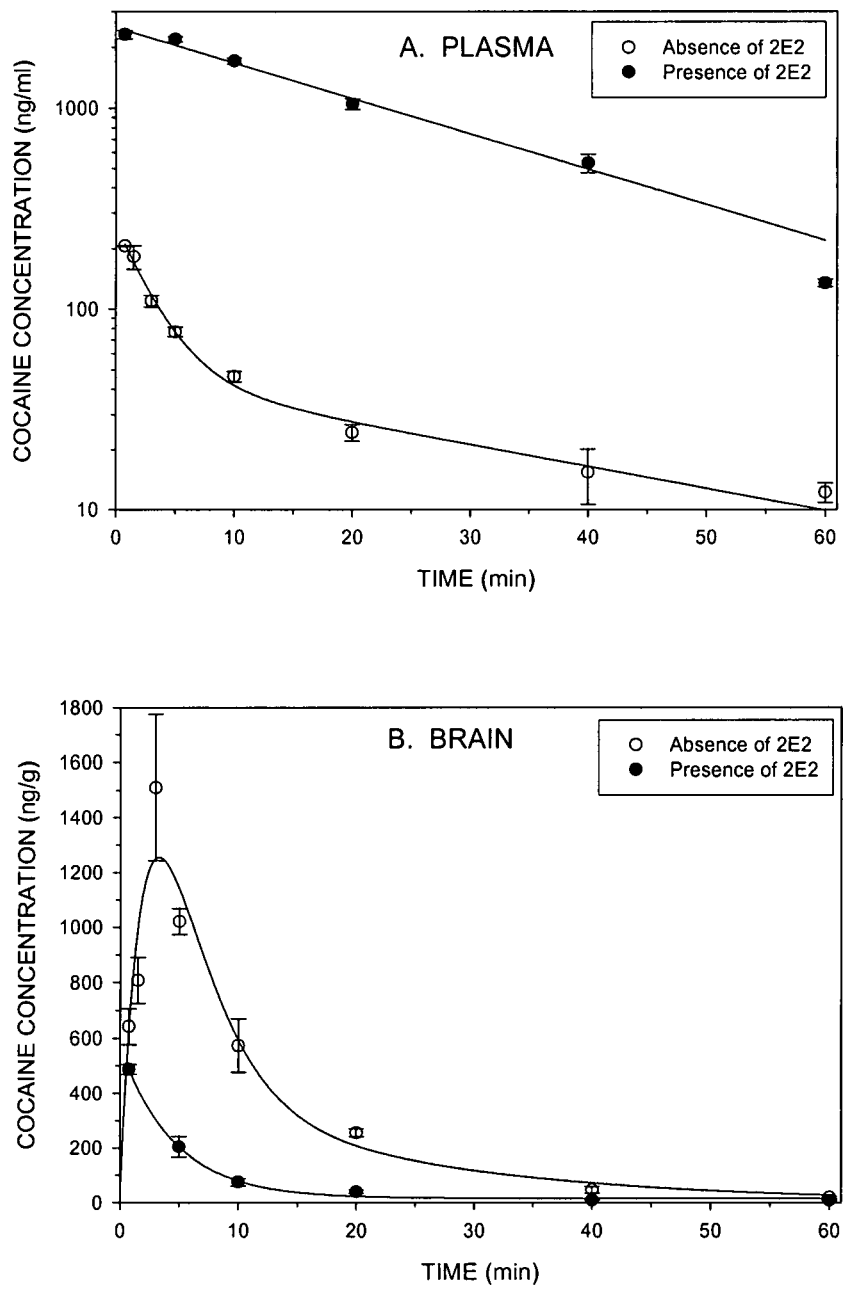
FIG. 4 is a graph which depicts the effect of 2E2 on the pharmacokinetics of cocaine in plasma (A) and brain (B) where mice receive an i.v. infusion of 120 mg/kg of 2E2, one hour later the mice receive an i.v. injection of cocaine HCl (0.56 mg/kg), and the animals are sacrificed at the indicated times and samples are collected; the cocaine concentrations are determined by GC/MS, the data points represent the mean±SEM from three mice and in the absence of 2E2 (open circles), the cocaine concentration-time profile in plasma (A) is described by a two-compartment pharmacokinetic model with a $t_{1/2\alpha}$ of 1.9 min and a $t_{1/2\beta}$ of 26.1 min, while in the presence of 2E2 (closed circles) a single compartment pharmacokinetic model indicated a $t_{1/2}$ of 17.1 min, in the brain (B) in the absence of 2E2 (open circles) a two-compartment pharmacokinetic model with first order input into the first compartment describes the cocaine concentration-time profile and the calculated input $t_{1/2}$ is 2.0 min and the $t_{1/2\alpha}$ and $t_{1/2\beta}$ values are 2.0 min and 14.5 min, respectively, and in the presence of 2E2 (closed circles), a single compartment pharmacokinetic model with first order elimination of cocaine indicates an elimination $t_{1/2}$ value of 3.8 min.

Next, the disposition of cocaine in mouse plasma subsequent to its i.v. injection via the jugular vein is determined. The highest plasma concentrations measured (~110 ng/ml) are observed at the earliest sample time, after which cocaine concentrations declined rapidly (FIG. 4A). A pharmacokinetic model assumes that cocaine distributed between a central and a peripheral compartment improves the fit to the observed data as compared to a single compartment model. This result is similar to that which has previously been reported for i.v. injected cocaine in several species including rats, non-human primates and for i.p. injected cocaine in mice. The simplest pharmacokinetic model that provides a general description of the data generated parameter estimates for the distribution half-life ($t_{1/2\alpha}$) and terminal elimination half-life ($t_{1/2\beta}$) for cocaine of 1.9 and 26.1 min, respectively. The calculated Vdss is 6.0 l/kg.

Effect of Cocaine-Specific mAbs on Cocaine Distribution.

In these experiments a single time point, 5 minutes after i.v. cocaine administration, is selected at which to determine the effect of circulating anti-cocaine mAbs on the in vivo plasma and brain levels of cocaine. As shown in Table 1 below, at 5 minutes considerable distribution of cocaine has occurred as the plasma concentration (~77 ng/ml) declines from an initial value of ~110 ng/ml (45 sec, FIG. 4A) and brain levels (~1070 ng/g) are about 10-fold higher than that in plasma. The presence of mAb 2E2 then produced a substantial 29-fold increase in plasma and an almost 5-fold decrease in brain cocaine concentrations (Table 1) in comparison to the vehicle controls. Furthermore, pretreatment with the mouse anti-cocaine mAbs 3P1A6 ($K_d$=0.2 nM) and B4E10 ($K_d$=40 nM,) also similarly increased cocaine concentrations in plasma, while they are somewhat less effective than 2E2 in decreasing cocaine concentrations in the brain. These results clearly demonstrate the capability of cocaine-specific mAbs for in vivo binding of cocaine. In contrast, the pretreatment with non-specific human polyclonal antibodies with no measurable affinity for cocaine produced a small increase in cocaine concentrations in both plasma and brain relative to those in mice pretreated with the vehicle (PBS).

TABLE 1

|  | Plasma cocaine concentration (ng/ml) | Change from vehicle | Brain cocaine concentration (ng/g) | Change from vehicle |
| --- | --- | --- | --- | --- |
| Vehicle | 76.6 ± 3.3 (n = 23) |  | 1070.5 ± 32.1 (n = 22) |  |
| Human IgG | 121.2 ± 5.6* (n = 6) | +1.6-fold | 1568 ± 130.5* (n = 5) | +1.5-fold |
| 2E2 | 2197.7 ± 75.8** (n = 6) | +28.7-fold | 223.7 ± 25.5** (n = 6) | −4.8-fold |
| 3P1A6 | 2215.5 ± 157.2** (n = 6) | +28.9-fold | 469.2 ± 68.9** (n = 6) | −2.3-fold |
| B4E10 | 1591.5 ± 57.8** (n = 6) | +20.8-fold | 560.5 ± 62.4** (n = 6) | −1.9-fold |

The Dose-Dependent Effect of 2E2 on Plasma and Brain Cocaine Concentrations.

Figure 2:
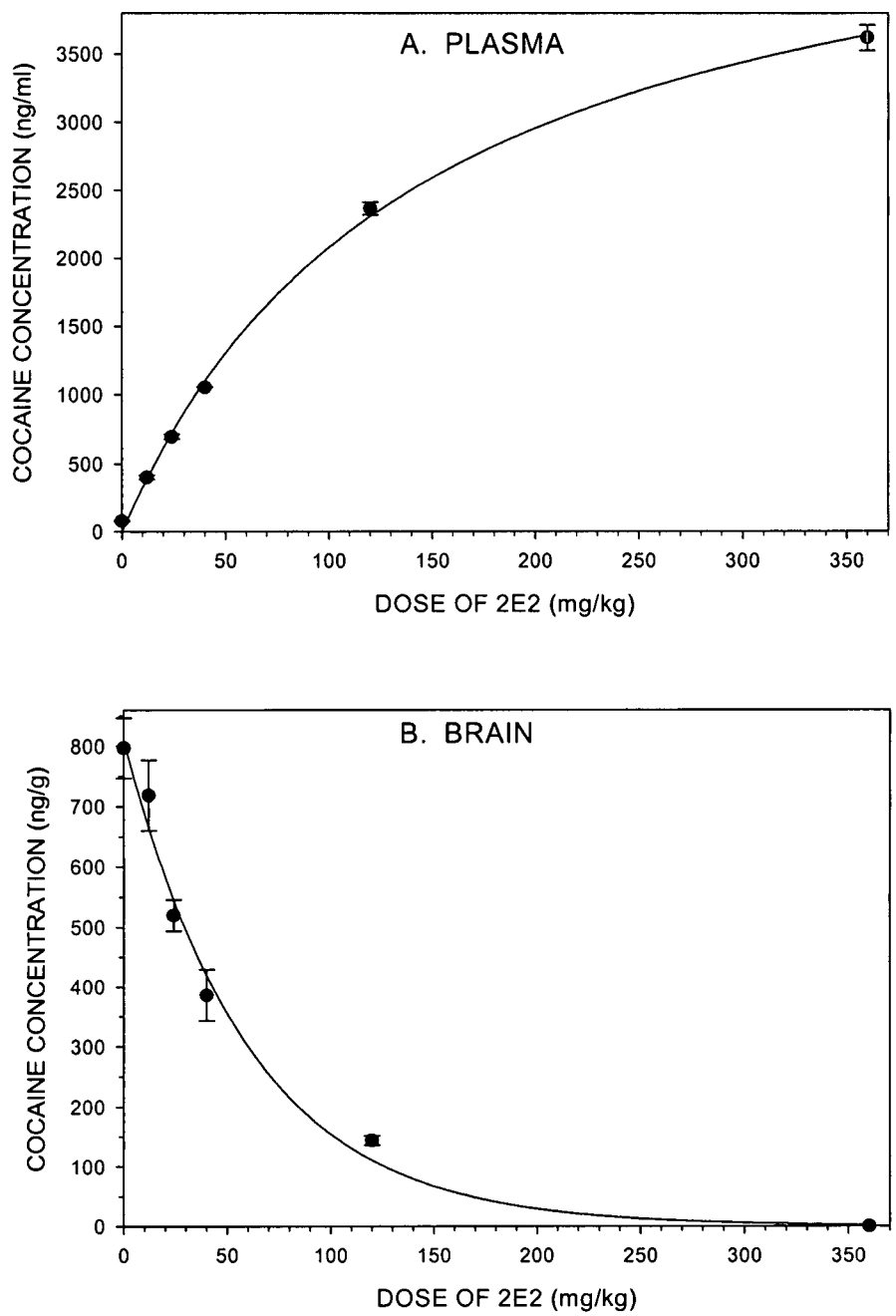
FIG. 2 is a graph which depicts the dose-dependent effect of 2E2 on plasma (A) and brain (B) concentrations of cocaine where mice are injected with vehicle or 2E2 at doses of 12, 24, 40, 120 or 360 mg/kg; one hour after the infusion of vehicle or 2E2 is completed an i.v. bolus of cocaine HCl is administered and after five minutes the samples are collected, cocaine concentrations are measured using GC/MS, symbols represent the mean±SEM from three mice, the line through the data points represents the best fit according to a hyperbolic function, and the $ED_{50}s$ of 2E2 for decreasing the cocaine concentration in the brain and increasing the plasma cocaine concentration are approximately 50 and 60 mg/kg, respectively.

In view of the magnitude of the effects of stoichiometric doses of the anti-cocaine mAbs on the plasma and brain cocaine concentrations, the dose-dependency for the responses is determined using mAb 2E2. In the absence of 2E2 the mean±SEM plasma cocaine concentration at 5 min post cocaine injection is 78.5±4.5 ng/ml (FIG. 2A). Infused 2E2 produces a dose-dependent increase in plasma cocaine concentrations (FIG. 2A). The lowest dose of 2E2 (12 mg/kg, a 1:10 mAb:cocaine ratio) produces a significant ($p<0.01$, one-way ANOVA with post-hoc test) 5.1-fold increase in plasma cocaine concentrations while the highest dose (360 mg/kg, a 3:1 ratio) produces a dramatic 46.1-fold increase in cocaine concentrations. The calculated dose of 2E2 that produces 50% of the highest effect for the range of 2E2 doses used ($ED_{50}$) is approximately 80 mg/kg, a somewhat less than stoichiometric amount of 2E2.

In the absence of 2E2 the mean±SEM brain cocaine concentration at 5 min post injection, corrected for cocaine present in cerebral blood, is 796.8±50 ng/ml (FIG. 2B). This represents a brain:plasma cocaine concentration ratio of 10:1. 2E2 then produces a dose-dependent decrease in brain cocaine concentrations (FIG. 2B). At the dose of 24 mg/kg, 2E2 produces a significant 35% decrease in cocaine concentrations. At the 2E2 dose of 360 mg/kg, after correction for cocaine present in the residual blood, the brain cocaine concentration is negligible. The $ED_{50}$ for the range of 2E2 doses used is approximately 60 mg/kg.

The Effect of 2E2 on Cocaine Metabolite Concentrations in Plasma and Brain.

Figure 3:
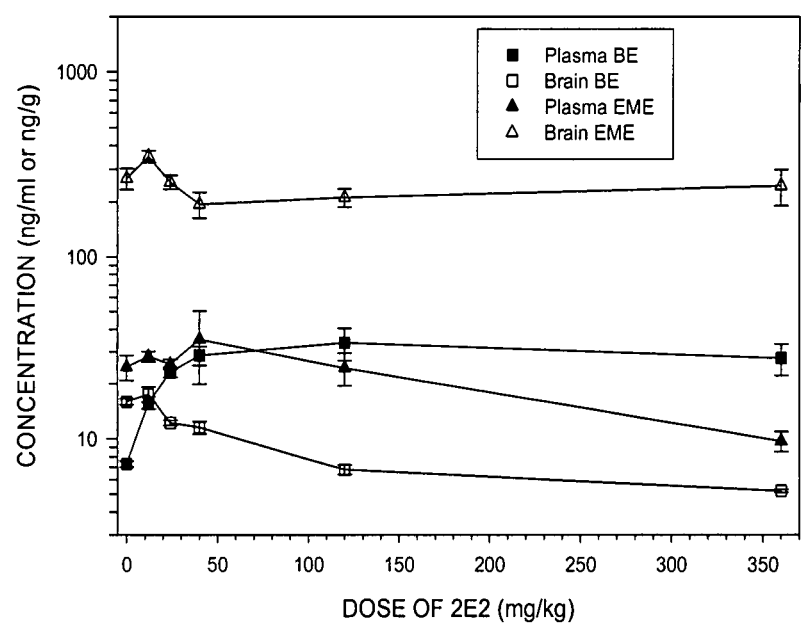
FIG. 3 is a graph which depicts the effect of 2E2 on plasma and brain concentrations of cocaine metabolites where the concentrations of BE and EME are measured in the same tissue samples used for FIG. 2; plasma and brain concentrations of BE are represented by closed and open squares, respectively, and plasma and brain concentrations of EME are represented by closed and open triangles, respectively.

An additional point of interest is the determination of the effects of circulating 2E2 on the in vivo metabolism of cocaine. As shown in FIG. 3, at 5 min after the injection of cocaine in the absence of 2E2, mean concentrations of the predominant cocaine metabolite in mice, EME, which results largely from plasma butyrylcholinesterase activity, are 25 ng/ml and 267 ng/g in plasma and brain, respectively. This represented a brain:plasma ratio for EME of 10.7:1, a ratio similar to that of cocaine in these mice (FIG. 2), thus the cocaine:EME ratio is ~3:1 in both plasma and brain. Produced by non-specific liver carboxylesterase activity, BE levels are lower with mean concentrations of 7 ng/ml and 16 ng/g in plasma and brain, respectively, representing a brain:plasma ratio of 2.3:1. A modest increase (~3-fold) in plasma BE concentrations is observed with increasing doses of 2E2 but the effect approached a plateau at 2E2 doses above 40 mg/kg. There is a concomitant decrease in brain BE concentrations which is observed at doses above 40 mg/kg. These results are consistent with mAb 2E2 having no effect on BE production but a sufficiently high affinity for BE to sequester some in the plasma, but its levels are limited. In contrast, plasma EME concentrations appear unaffected at the lower doses of 2E2, but an approximate 2-fold reduction is observed at the highest dose of 2E2. There is no systematic effect of 2E2 dose on brain EME concentrations (FIG. 3). It is of note, that despite 2E2's effective in vivo binding of cocaine, its alterations in cocaine's initial metabolism appear modest.

Effect of 2E2 on the Pharmacokinetics of Cocaine in Plasma and Brain.

Next, the effects of a stoichiometric dose of 2E2 on the pharmacokinetics of a single injection of cocaine are determined. As shown in FIG. 4A, in the presence of 2E2, the peak plasma concentrations (~1,100 ng/ml) of cocaine are observed at the earliest time point (45 sec) sampled after its injection. This is similar to what is observed in the absence of 2E2. However, the peak plasma concentration is 11.3-fold higher in the presence than in the absence of 2E2. Furthermore, in contrast to the biexponential decrease in the concentrations of cocaine observed in the absence of 2E2, the decrease in the cocaine concentration is well described by a pharmacokinetic model that assumes a single compartment and no initial distribution phase. Thus, the calculated $t_{1/2}$ for the disappearance of cocaine from plasma in the presence of 2E2 is 17.1 min and this contrasts with the distribution and elimination phases, with parameter estimates for $t_{1/2\alpha}$ and $t_{1/2\beta}$ of 1.9 and 26 min, respectively. 2E2 also produces a sustained increase in the plasma cocaine concentration that results in 26-fold increase in the area under the concentration-time curve (AUC) in plasma. Consistent with this result, the calculated Vdss of cocaine in the presence of 2E2 is 0.2 l/kg as compared to 6.0 l/kg in the absence of 2E2.

As shown in FIG. 4B, the cocaine concentration-time profile in brain differs substantially from that observed in the plasma (FIG. 3A). The concentration of cocaine in the brain (corrected for cocaine present in residual blood) at 45 sec (~650 ng/g) after the injection is approximately 6-fold higher than that measured in plasma. The brain cocaine concentrations subsequently increase further and the highest measured concentration is observed at 3 min (~1,500 ng/g), after which concentrations then rapidly decline. A pharmacokinetic model that assumes a first-order input to the brain and a first-order output is used to describe the increase and subsequent decrease in brain cocaine concentrations. The estimated $t_{1/2}$ for entry into the brain is approximately 2.0 min. Furthermore, a pharmacokinetic model assuming two compartments described the disappearance of cocaine from the brain. The parameter estimates for $t_{1/2\alpha}$ and $t_{1/2\beta}$ are 2.0 min and 14.5 min, respectively (FIG. 4B), values similar to those obtained for the plasma.

In the presence of 2E2, the peak cocaine concentration (~490 ng/g) is observed at the earliest sample time and it subsequently declines rapidly over time (FIG. 4B). There is no indication of the normal delayed influx and peak of the cocaine concentrations in the brain and a single compartment model approximates the decline in cocaine concentrations. The estimated $t_{1/2}$ is 3.8 min, a value considerably faster than the $t_{1/2\beta}$ value obtained in the absence of 2E2.

Importantly, 2E2 produces an approximately 4.5-fold (78%) decrease in the cocaine AUC in the brain.

Discussion

The low volume of distribution of 2E2 observed in mice is similar to that previously reported for several murine and rat monoclonal IgG$_1$ antibodies and human polyclonal IgG$_1$ antibodies in rats and is consistent with 2E2's distribution being predominantly restricted to the blood volume. Additionally, the elimination $t_{1/2}$ value for 2E2 is relatively long and similar to that reported for other murine, rat and human antibodies in rats. This indicates that 2E2's effects on cocaine pharmacokinetics could persist for several days after a single injection. Furthermore, the terminal elimination $t_{1/2}$ of cocaine is more than 400-fold faster than that of 2E2 and, therefore, it can be assumed that the plasma concentration of 2E2 is constant during the study of cocaine pharmacokinetics. Interestingly, although the $V_d$ and $t_{1/2}$ for 2E2 are similar to those previously described for antibodies in rodents, there is no evidence for an initial distribution of 2E2 from the blood to the interstitial spaces.

As to 2E2's in vivo binding of cocaine, its effect on the plasma concentration of cocaine is saturable, which is consistent with the limited number of cocaine molecules present. Furthermore, doses of 2E2 that are only 10% to 30% of the dose of cocaine still provide a measurable increase in plasma cocaine concentrations and a decrease in exposure of the brain to cocaine. This is consistent with reports that a 0.3 molar ratio of anti-phencyclidine (PCP) Fabs decreases the behavioral effects of PCP in rats. Furthermore, a 4 mg dose of an anti-cocaine mAb, representing a molar ratio of approximately 0.005, has been reported to antagonize the behavioral effects of repeated 1 mg/kg doses of cocaine HCl. While, 30 and 40 mg/kg doses of another murine anti-cocaine mAb decrease the self-administration of cocaine at molar ratios of approximately 0.2 for each cocaine injection. The finding that 2E2 produces a substantial reduction in the brain's exposure to cocaine at equimolar ratios and has measurable effectiveness at lower molar ratios indicates that 2E2 will reduce brain concentrations even after a mAb dose has been partially eliminated. Thus the efficacy of a given dose of 2E2 is prolonged.

The demonstration that an equimolar dose of a nonspecific antibody did not significantly alter either plasma or brain concentrations of cocaine rules out the possibility of nonspecific effects of infused IgG proteins as an explanation for the mAb effects on cocaine pharmacokinetics. Therefore, the efficacy of anti-cocaine mAbs requires specificity of the binding interaction between the drug/antibody molecules. However, the three anti-cocaine mAbs with affinities ranging from very high ($K_d$=0.2 nM) to modest ($K_d$=40 nM, as measured in vitro at equilibrium) are approximately equipotent under the limited in vivo experimental conditions tested. This suggests that the ability of an antibody to influence the pharmacokinetics of cocaine may not be highly affinity sensitive. Therefore, antibodies with a fairly broad range of affinities may have clinical efficacy. Antibodies with low affinity, that is having $K_d$ s in the µM range, have been reported to ameliorate some behavioral effects of cocaine in rodents, but would most likely not be as effective as 2E2 on treating cocaine-related disorders.

In the presence of 2E2, the initially observed approximately 10-fold increase in the concentration of cocaine in plasma, the lack of an initial distribution phase from the plasma and the reduction of the Vdss of cocaine to essentially that of 2E2 are all consistent with 2E2 restricting cocaine's distribution predominantly to the blood volume. Therefore, the 2E2-induced decrease in brain cocaine concentrations is due to an inhibition of cocaine distribution from the blood to the brain. Furthermore, the reduction in the peak levels and the distribution of cocaine to the brain occurs at all time points, indicating that 2E2 did not simply delay cocaine's distribution to the brain. This report is the first to demonstrate that an anti-cocaine mAb can prevent the entry of cocaine into the brain and it is consistent with previous reports that active immunization-induced anti-cocaine antibodies decrease cocaine levels in brain after i.v., intranasal or i.p. cocaine administration. The ability of 2E2 to decrease brain concentrations of cocaine is also consistent with the mAb-induced reductions observed for other psychoactive drugs such as phencyclidine, methamphetamine and nicotine in rats.

The markedly altered distribution of cocaine is the result of cocaine binding to 2E2. While it may initially be believed that this mAb binding of cocaine also restricts cocaine's access to the enzymes that metabolize it, thereby decreasing its clearance, there is no evidence of an increase in the elimination $t_{1/2}$ of cocaine in plasma. This is consistent with the reported lack of effect of active immunization on either the elimination of cocaine from plasma or on the rate of metabolism of nicotine. However, a murine anti-nicotine mAb and active immunization against nicotine have also been reported to significantly increase the elimination $t_{1/2}$ of nicotine in rats. The reasons for these discrepant results are not clear at present but do not appear to be related to different affinities of the mAbs or the polyclonal antibodies for their target molecules. If anti-drug antibodies can inhibit the metabolism and slow the rate of drug elimination this would increase the in vivo concentrations resulting from repeated drug doses and may not be desirable for an immunotherapeutic agent. Importantly, the lack of effect of 2E2 on cocaine elimination from plasma should minimize the potential for 2E2 to become saturated following repeated doses of cocaine.

In summary, the high affinity anti-cocaine mAb 2E2 limits the distribution of cocaine to the plasma thus decreasing the levels of cocaine reaching the brain without any detectable effect on the rate of elimination of cocaine. The data further supports the general concept of the usefulness of immunotherapy for the treatment of drug abuse and is consistent with mAb 2E2 being effective as a passive immunotherapy for the prevention of relapse in cocaine abuse.

The foregoing description of various embodiments and principles of the invention has been presented for the purposes of illustration and description. It is not intended to be exhaustive or to limit the inventions to the precise forms disclosed. Many alternatives, modifications, and variations will be apparent to those skilled the art. Moreover, although multiple inventive aspects and principles have been presented, these need not be utilized in combination, and various combinations of inventive aspects and principles are possible in light of the various embodiments provided above. Accordingly, the above description is intended to embrace all possible alternatives, modifications, aspects, combinations, principles, and variations that have been discussed or suggested herein, as well as all others that fall within the principles, spirit and scope of the inventions as defined by the claims.

What is claimed is:

1. A method for treating a cocaine-related disorder in an individual, comprising administering to the individual a therapeutic amount of a monoclonal antibody comprising a human gamma heavy chain and a murine lambda light chain, wherein the antibody specifically binds cocaine and is generated by immunizing a HCo7/Ko5 mouse with an antigen comprising a conjugate of benzoylecgonine and an immunogenic carrier protein, wherein the murine lambda light chain comprises SEQ ID NO: 4, SEQ ID NO: 5, and SEQ ID NO: 6 and wherein the human gamma heavy chain comprises SEQ ID NO: 7, SEQ ID NO: 8, and SEQ ID NO: 9, wherein the antibody binds cocaine or a derivative thereof.

2. The method of claim 1, wherein the murine lambda light chain comprises a murine variable region and a human constant region.

3. The method of claim 1, wherein the murine lambda light chain comprises SEQ ID NO: 1.

4. The method of claim 1, wherein the antibody has at least a nanomolar affinity for cocaine.

5. The method of claim 1, wherein the antibody has a $K_d$ of about 40 nM or less.

6. The method of claim 5, wherein the antibody has a $K_d$ of about 4 nM.

7. The method of claim 1, wherein the cocaine-related disorder comprises at least one of overdose, addiction, dependence, and relapse.

8. The method of claim 1, wherein the human gamma heavy chain comprises SEQ ID NO: 2.

9. The method of claim 8, wherein the murine lambda light chain comprises SEQ ID NO: 1.

10. The method of claim 1, wherein the murine lambda light chain comprises a murine variable region and a murine constant region.

11. A monoclonal antibody comprising a human gamma heavy chain and a murine lambda light chain, wherein the antibody specifically binds cocaine and is generated by immunizing a HCo7/Ko5 mouse with an antigen comprising a conjugate of benzoylecgonine and an immunogenic carrier protein, wherein the murine lambda light chain comprises SEQ ID NO: 4, SEQ ID NO: 5, and SEQ ID NO: 6 and wherein the human gamma heavy chain comprises SEQ ID NO: 7, SEQ ID NO: 8, and SEQ ID NO: 9.

12. The monoclonal antibody of claim 11, wherein the murine lambda light chain comprises SEQ ID NO: 1.

13. The monoclonal antibody of claim 11, wherein the human gamma heavy chain comprises SEQ ID NO: 2.

14. The monoclonal antibody of claim 11, wherein the murine lambda light chain comprises a murine variable region and a murine constant region.

15. The monoclonal antibody of claim 11, wherein the murine lambda light chain comprises a murine variable region and a human constant region.

16. A method for binding cocaine or a derivative thereof comprising contacting cocaine or a derivative thereof with an effective amount of a monoclonal antibody comprising a human gamma heavy chain and a murine lambda light chain, wherein the antibody specifically binds cocaine and is generated by immunizing a HCo7/Ko5 mouse with an antigen comprising a conjugate of benzoylecgonine and an immunogenic carrier protein, wherein the murine lambda light chain comprises SEQ ID NO: 4, SEQ ID NO: 5, and SEQ ID NO: 6 and wherein the human gamma heavy chain comprises SEQ ID NO: 7, SEQ ID NO: 8, and SEQ ID NO: 9.

* * * * *

UNITED STATES PATENT AND TRADEMARK OFFICE
CERTIFICATE OF CORRECTION

| | | |
|---|---|---|
| PATENT NO. | : 9,758,593 B2 | Page 1 of 1 |
| APPLICATION NO. | : 11/788808 | |
| DATED | : September 12, 2017 | |
| INVENTOR(S) | : Andrew B. Norman et al. | |

It is certified that error appears in the above-identified patent and that said Letters Patent is hereby corrected as shown below:

In the Specification

In Column 1, Line 10, before the FIELD OF THE INVENTION, insert:
--STATEMENT REGARDING FEDERALLY SPONSORED RESEARCH OR DEVELOPMENT
This invention was made with government support under DA012043 awarded by the National Institutes of Health. The government has certain rights in the invention.--

Signed and Sealed this
Twenty-third Day of April, 2024

Katherine Kelly Vidal
*Director of the United States Patent and Trademark Office*

SEQUENCE LISTING

<160> NUMBER OF SEQ ID NOS: 14

<210> SEQ ID NO 1
<211> LENGTH: 214
<212> TYPE: PRT
<213> ORGANISM: Murine

<400> SEQUENCE: 1

Gln Ala Val Val Ile Gln Glu Ser Ala Leu Thr Thr Ser Pro Gly Gly
1               5                   10                  15

Thr Val Ile Leu Thr Cys Arg Ser Ser Thr Gly Thr Ile Thr Thr Ser
            20                  25                  30

Asn Tyr Ala Asn Trp Val Gln Lys Lys Pro Asn His Val Phe Thr Gly
        35                  40                  45

Leu Ile Gly Ala Thr Ser Ile Arg Ala Pro Gly Val Pro Val Arg Phe
    50                  55                  60

Ser Gly Phe Leu Ile Gly Gly Lys Ala Ala Leu Thr Ile Thr Gly Ala
65                  70                  75                  80

Gln Thr Glu Asp Asp Ala Met Tyr Phe Cys Ala Leu Trp Tyr Asn Thr
                85                  90                  95

His Tyr Val Phe Gly Gly Gly Thr Lys Val Thr Val Leu Gly Gln Pro
            100                 105                 110

Lys Ser Thr Pro Thr Leu Thr Val Phe Pro Pro Ser Ser Glu Glu Leu
        115                 120                 125

Lys Glu Asn Lys Ala Thr Leu Val Cys Leu Ile Ser Asn Phe Ser Pro
130                 135                 140

Ser Gly Val Thr Val Ala Trp Lys Ala Asn Gly Thr Pro Ile Thr Gln
145                 150                 155                 160

Gly Val Asp Thr Ser Asn Pro Thr Lys Glu Gly Asn Lys Phe Met Ala
                165                 170                 175

Ser Ser Phe Leu His Leu Thr Ser Asp Gln Trp Arg Ser His Asn Ser
            180                 185                 190

Phe Thr Cys Gln Val Thr His Glu Gly Asp Thr Val Glu Lys Ser Leu
        195                 200                 205

Ser Pro Ala Glu Cys Leu
    210

<210> SEQ ID NO 2
<211> LENGTH: 442
<212> TYPE: PRT
<213> ORGANISM: Human

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Asp
            20                  25                  30

Trp Met Asn Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
    50                  55                  60

Lys Gly Arg Phe Thr Ile Ser Arg Asp Asn Ala Gln Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Glu Leu Gly Pro Trp Gly Gln Gly Thr Leu Val Thr Val Ser

```
            100                 105                 110
Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly
        435                 440

<210> SEQ ID NO 3
<211> LENGTH: 215
<212> TYPE: PRT
<213> ORGANISM: Human

<400> SEQUENCE: 3

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

```
Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Ala Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Arg Ser Asn Trp Pro Arg
                 85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 4
<211> LENGTH: 14
<212> TYPE: PRT
<213> ORGANISM: Murine

<400> SEQUENCE: 4

Arg Ser Ser Thr Gly Thr Ile Thr Thr Ser Asn Tyr Ala Asn
 1               5                   10

<210> SEQ ID NO 5
<211> LENGTH: 7
<212> TYPE: PRT
<213> ORGANISM: Murine

<400> SEQUENCE: 5

Ala Thr Ser Ile Arg Ala Pro
 1               5

<210> SEQ ID NO 6
<211> LENGTH: 9
<212> TYPE: PRT
<213> ORGANISM: Murine

<400> SEQUENCE: 6

Ala Leu Trp Tyr Asn Thr His Tyr Val
 1               5

<210> SEQ ID NO 7
<211> LENGTH: 6
<212> TYPE: PRT
<213> ORGANISM: Human

<400> SEQUENCE: 7

Ser Asp Trp Met Asn Trp
 1               5
```

<210> SEQ ID NO 8
<211> LENGTH: 17
<212> TYPE: PRT
<213> ORGANISM: Human

<400> SEQUENCE: 8

Asn Ile Asn Gln Asp Gly Ser Glu Lys Tyr Tyr Val Asp Ser Val Lys
1               5                   10                  15

Gly

<210> SEQ ID NO 9
<211> LENGTH: 4
<212> TYPE: PRT
<213> ORGANISM: Human

<400> SEQUENCE: 9

Glu Leu Gly Pro
1

<210> SEQ ID NO 10
<211> LENGTH: 11
<212> TYPE: PRT
<213> ORGANISM: Human

<400> SEQUENCE: 10

Arg Ala Ser Gln Ser Val Ser Ser Tyr Leu Ala
1               5                   10

<210> SEQ ID NO 11
<211> LENGTH: 7
<212> TYPE: PRT
<213> ORGANISM: Human

<400> SEQUENCE: 11

Gly Ala Ser Ser Arg Ala Thr
1               5

<210> SEQ ID NO 12
<211> LENGTH: 10
<212> TYPE: PRT
<213> ORGANISM: Human

<400> SEQUENCE: 12

Gln Gln Arg Ser Asn Trp Pro Arg Tyr Thr
1               5                   10

<210> SEQ ID NO 13
<211> LENGTH: 10
<212> TYPE: PRT
<213> ORGANISM: Human

<400> SEQUENCE: 13

Gln Leu Tyr Gly Ser Ser Leu Arg Tyr Thr
1               5                   10

<210> SEQ ID NO 14
<211> LENGTH: 215
<212> TYPE: PRT
<213> ORGANISM: Human

<400> SEQUENCE: 14

Glu Ile Val Leu Thr Gln Ser Pro Gly Thr Leu Ser Leu Ser Pro Gly
1               5                   10                  15

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Leu Tyr Gly Ser Ser Leu Arg
                85                  90                  95

Tyr Thr Phe Gly Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr Lys
            195                 200                 205

Ser Phe Asn Arg Gly Glu Cys
210                 215
```